(12) United States Patent
Smith

(10) Patent No.: US 9,585,378 B2
(45) Date of Patent: Mar. 7, 2017

(54) DISPOSABLE SINGLE-USE ANIMAL ATTRACTANT DISPENSING DEVICE

(71) Applicant: Barry Arlen Smith, Loudon, TN (US)

(72) Inventor: Barry Arlen Smith, Loudon, TN (US)

( * ) Notice: Subject to any disclaimer, the term of this patent is extended or adjusted under 35 U.S.C. 154(b) by 150 days.

(21) Appl. No.: 14/203,759

(22) Filed: Mar. 11, 2014

(65) Prior Publication Data

US 2014/0252110 A1   Sep. 11, 2014

Related U.S. Application Data

(60) Provisional application No. 61/775,842, filed on Mar. 11, 2013.

(51) Int. Cl.
*A01M 31/00* (2006.01)
*A01M 1/20* (2006.01)
*A61L 9/04* (2006.01)

(52) U.S. Cl.
CPC ........ *A01M 31/008* (2013.01); *A01M 1/2044* (2013.01); *A61L 9/04* (2013.01)

(58) Field of Classification Search
CPC .............. A01M 31/008; A01M 1/2044; A01M 1/2055; A61L 9/04; A61L 9/12; A61L 9/127
USPC ...................................... 239/6, 34–60; 43/1
See application file for complete search history.

(56) References Cited

U.S. PATENT DOCUMENTS

| | | | |
|---|---|---|---|
| 4,186,502 A | 2/1980 | Foster | |
| 4,682,715 A | 7/1987 | Reeves | |
| 4,722,477 A | 2/1988 | Floyd | |
| 4,735,010 A | 4/1988 | Grinarml | |
| 4,809,455 A | 3/1989 | Smart | |
| 5,074,439 A * | 12/1991 | Wilcox | ............... A01M 31/008 206/38 |
| D351,934 S | 11/1994 | Devoe | |
| 5,369,903 A | 12/1994 | Cox | |

(Continued)

OTHER PUBLICATIONS

Tink's Hot Bomb #69 Doe-In-Rut Buck Lure Disposable Heated Lure Dispenser; http//www.bizrate.com/hunting-archery-equipment/2330592147.html. It is not known whether or not this reference is prior art or not. However, it is requested to be considered as prior art for the purposes of examination only.

*Primary Examiner* — Arthur O Hall
*Assistant Examiner* — Juan C Barrera
(74) *Attorney, Agent, or Firm* — Luedeka Neely Group, P.C.

(57) ABSTRACT

A disposable single-use animal attractant dispensing device has a pouch formed by front and back panels joined along peripheral edges, which includes a pouch section for retaining an animal attractant and a single-use absorbent lure for absorbing the attractant. A first opening formed by un-joined portions of the panels is sealed together along with a portion of the lure to form a sealing section, forming a substantially impervious seal. A notch is provided to assist the user in rupturing the seal to separate the pouch and sealing sections and to expose the lure. A securement is provided for securing the pouch to a user, and may include a pouch connection member and a user connection member. An aperture disposed in the sealing section of the pouch receives a portion of the securement. A pocket on an outer surface of the pouch holds a portion of the securement.

8 Claims, 6 Drawing Sheets

(56) References Cited

U.S. PATENT DOCUMENTS

| | | | | |
|---|---|---|---|---|
| 5,622,314 | A | * | 4/1997 | Eason ........................ A61L 9/12 239/44 |
| 5,656,282 | A | | 8/1997 | Cook |
| 5,672,342 | A | | 9/1997 | Bell |
| 5,916,552 | A | * | 6/1999 | Perry ..................... A01K 15/02 424/400 |
| 5,987,800 | A | * | 11/1999 | Regan ................. A01M 31/008 43/1 |
| 6,557,778 | B1 | * | 5/2003 | Shiffler ............... A01M 1/2055 239/53 |
| 6,676,033 | B1 | * | 1/2004 | Campesi, Sr. ...... A01M 31/008 239/44 |
| 7,093,770 | B1 | * | 8/2006 | Moran ................... A01K 15/02 206/37 |
| 7,273,184 | B2 | | 9/2007 | Brown |
| 2003/0175320 | A1 | * | 9/2003 | Weiser .................. A01N 25/34 424/411 |
| 2006/0289668 | A1 | | 12/2006 | Szymczak |

\* cited by examiner

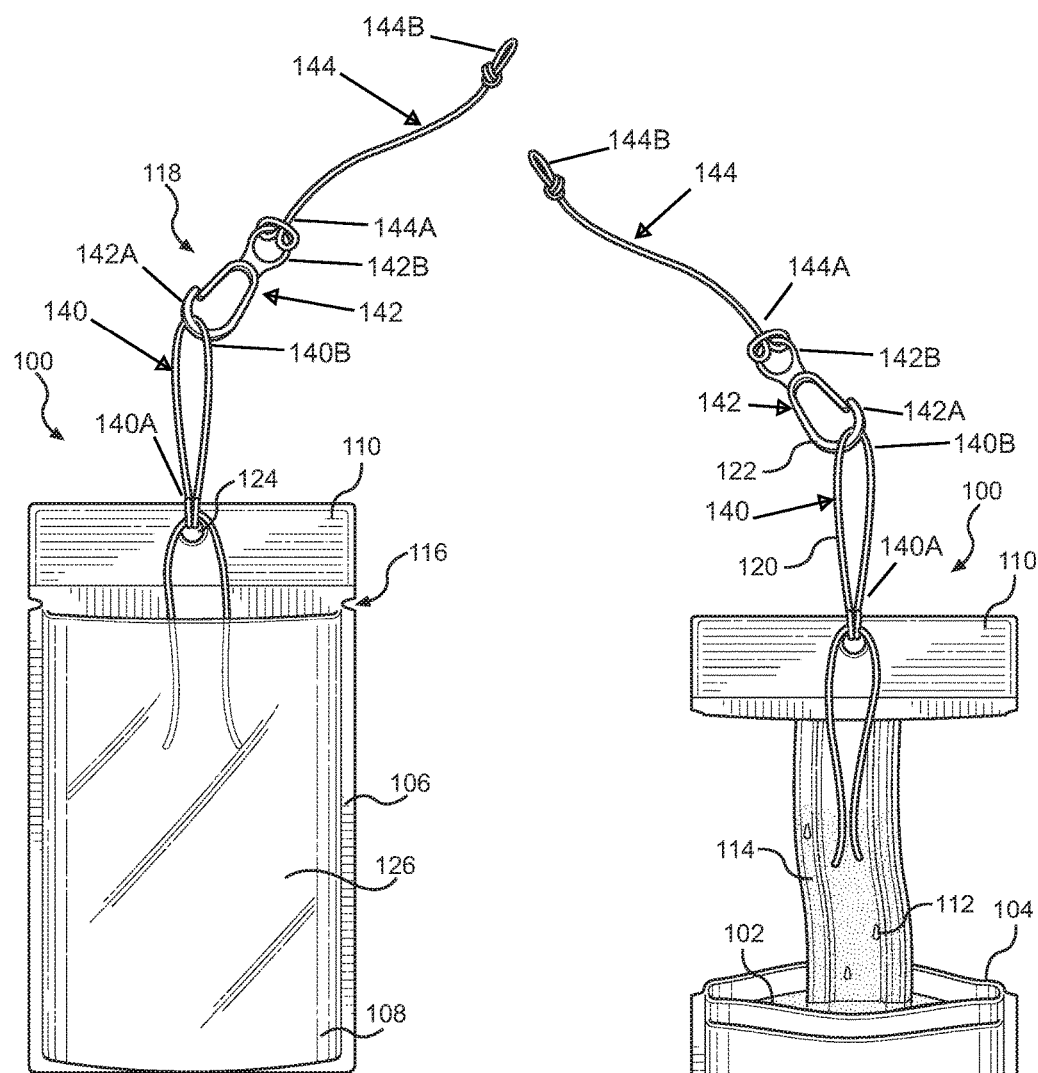

DISPOSABLE SINGLE-USE ANIMAL ATTRACTANT DISPENSING DEVICE

CROSS-REFERENCE TO RELATED APPLICATIONS

This application claims the benefit of U.S. Provisional Application No. 61/775,842, filed Mar. 11, 2013.

FIELD

The present invention relates generally to the field of hunting and trapping and, more particularly, relates to a disposable single-use animal attractant dispensing devices.

BACKGROUND

In watching, hunting and trapping animals, it is often useful to disperse a scent into the air or onto the surrounding areas. This may be done for a number of reasons. One reason is to conceal the hunter's own scent so as to avoid alerting animals to the hunter's presence. Another reason is that certain scents may, in fact, lure the animal to a particular location. Additionally, mobility is often desirable and required in order to track and trap animals. However, this may leave a scent trail so stationary scents are often inadequate. It is often preferred to avoid contact with the scent and that the scent not contact the hunter's person, clothing, equipment, etc. It is also preferable that the device be simple and quick to use, easy replenished and easily disposed of without requiring long-term storage after opening. Finally, it is also desired that the scent-dispersing device be able to disperse the scent automatically with little or no effort by the user.

Therefore, what is needed is a single-use animal attractant-dispensing device that is simple and easy to use, may be mobile, disperses the scent automatically, and is easily disposed of and replaced.

SUMMARY

The above and other needs are met by a disposable single-use animal attractant-dispensing device. The device includes front and back panels, which may be formed from a material substantially impervious to liquids. The pouch may be formed using a material that is substantially impervious to at least one of ultraviolet radiation and visible light.

The panels are positioned in face-to-face relationship and peripheral edges of the panels are joined together to define a disposable single-use pouch. The pouch includes a pouch section for retaining the animal attractant defined by a section of the peripheral edges of the front and back panels joined together. The pouch section also includes a first opening defined by a section of the peripheral edges of the front and back panels not joined together. A sealing section is formed by sealing together the peripheral edges and a section of the front and back panels located at the first opening.

The pouch includes a rupturable seal that is located between the sealing section and the pouch section. The seal permits the sealing section to be removed from the pouch section, thereby exposing the first opening of the pouch section. The device may also include a tear notch that is located in at least one of the peripheral edges of the joined front and back panels adjacent the rupturable seal. The tear notch assists the user in rupturing the rupturable seal and in separating the pouch section from the sealing section.

The device also has a quantity of animal attractant disposed in the pouch section. A disposable single-use lure is placed within the pouch. The animal attractant may include animal urine, such as deer urine. The lure may include a moisture absorbent material for absorbing at least a portion of the quantity of a liquid animal attractant. However, certain man-made attractants are in powder form rather than liquid and would also be suitable for the pouch. A section of the lure is sealed between the front and back panels of the sealing section such that the lure is removed from the pouch section when the sealing section is separated from the pouch section.

A securement is provided for removably securing the pouch to a user. The device may also include an aperture disposed in the sealing section of the pouch for receiving and fixedly connecting the securement to the pouch. The securement may include a lanyard or length of rope or string for removably securing the pouch to a user. The device may also include a pocket formed on an outer surface of at least one of the front and back panels for receiving and securely holding at least a section of the securement.

The device may also allow for easy use and exchange of multiple pouches. In particular, the device may include a pouch connection member that connects to the pouch and a user connection member that connects to a user. The pouch is then connected to the user by connecting the pouch connection member and user connection member together. After a first pouch has been used by the user, it may be replaced by disconnecting the pouch and the user connection members and then re-connecting the pouch connection member of a second pouch to the user connection member. Pouches may be provided with the pouch connection member already attached to the pouch. Additionally, multiple pouches may be sold together and may also include a single user connection member.

Further details of each of these and other embodiments of the invention are provided in the drawings and in the detailed description.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 2 is a front elevation view depicting a disposable single-use animal attractant dispensing device in accordance with an embodiment of the present disclosure;

FIG. 3 is depicts the disposable single-use animal attractant dispensing device shown in FIG. 2 after the rupturable seal has been broken and the pouch section is separated from the sealing section;

FIG. 3 is a perspective view of the device of FIG. 1, wherein the pouch section has been separated from the sealing section via the rupturable seal and the lure is partially removed from the pouch section;

DETAILED DESCRIPTION

Figure 1:
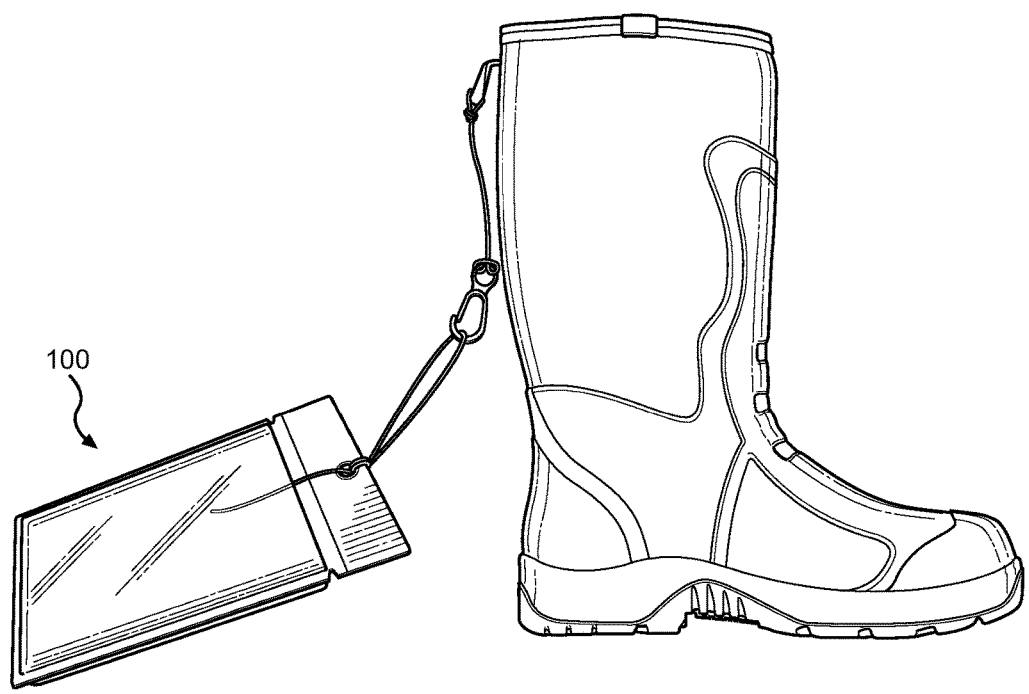
FIG. 1 is a front elevation view depicting a disposable single-use animal attractant dispensing device attached to a shoe in accordance with an embodiment of the present disclosure.

In the description with follow, like parts are marked throughout the specification and drawings with the same reference numerals, respectively. The drawings are not necessarily to scale and the proportions of certain parts have been exaggerated and/or shown in schematic form in the interest of clarity and conciseness.

Throughout this description, the term "attractant" is often used. This term is used as a shorthand method of referring to animal scents, attractants and baits, such as animal urine and the like, whose purpose is to attract animals, but also to scent covers, whose purpose is to conceal scents left by the hunter. These covers may include, for example, acorn, pine, earth, and other similar scents. Additionally, attractants may be provided in solid form, including as a power, in liquid form, or in a combination.

With reference now to the figures and, in particular, to FIGS. 1-3, there is provided a disposable single-use animal attractant dispensing device, generally referred to herein as a pouch 100. The pouch 100 is designed to dispense an animal attractant so as to attract an animal to a hunter or trapper's location. In certain embodiments, the pouch 100 may be worn on a section of a shoe or boot or at the lower end of the pants leg of a user. A section of the device drags behind the user and dispenses an attractant onto a ground surface, surrounding natural features, or into the atmosphere as the user walks.

Users may prefer to minimize contact with certain animal attractants, such as animal urine. Accordingly, unlike other attractant dispensing devices, which are reloaded/refilled, cleaned, etc. after each use, the pouch 100 of the present disclosure is a single use, disposable pouch that is ready for use immediately upon opening the sealed pouch, requiring no additional preparation steps, and may be disposed of after a single use.

The pouch 100 includes a front panel 102 and a back panel 104, which are preferably formed from a material impervious to liquids. Additionally, because certain attractants or scents may degrade when exposed to certain types of radiation, the panels may be formed from materials designed to inhibit the transmission of such radiation into the pouch 100. For example, the panels are formed using a material that is substantially impervious to at least one of ultraviolet radiation and visible light.

The panels 102, 104 are disposed in face-to-face relationship with a section of a peripheral edge 106 of each of the panels joined together to define a disposable single-use pouch. The pouch includes a pouch section 108 and a sealing section 110 for sealing the pouch section. The pouch section 108 is defined by a section of the peripheral edges 106 of the front panel 102 and back panel 104 that have been joined together.

An animal attractant 112 such as animal urine (e.g., deer, bear, boar, etc.) or other scents may be placed into the pouch section 108. Additionally, a lure 114 may be inserted into the pouch section 108 between the panels 102, 104 to absorb at least a portion of the attractant 112. The lure 114 is comprised of an absorbent material, such as a piece of cloth, that is designed to absorb either liquid or solid animal attractant or both.

The exact composition, size and configuration of the lure 114 allow it to absorb and retain a quantity of the attractant 112 sufficient to disseminate an effective quantity of attractant on a ground surface, other natural features, such as trees, bushes, etc., or into the surrounding atmosphere, so as to attract an animal to a hunter's or trapper's location.

In manufacturing the pouch 100, a section of the pouch section 108 may be left temporarily unsealed such that an attractant as previously described may be easily placed into the pouch section and/or to insert other items, such as the lure 114, into the pouch section. The lure 114 is inserted into the pouch section 108 such that a section of the lure is submerged in the attractant 112 and such that another section of the lure is near the unsealed section of the pouch. The lure 114 and the remaining section of the unsealed section of the peripheral edge 106 are then sealed together, such that one end of the lure 114 is secured in the sealing section 110 of the pouch 100.

The sealing section 110 provides a leak-proof, preferably odor-proof, seal at the opening in the pouch section 108. As shown in FIGS. 2 and 3, the seal is a rupturable seal that may be ruptured by a user in order to separate the pouch section 108 from the sealing section 110 in order to expose the lure 114 and to withdraw it from the pouch section for use. Additionally, the pouch 100 may be provided with one or more notches 116 disposed in the peripheral edges 106 of the pouch 100 for assisting the user in separating the pouch section 108 from the sealing section 110.

The pouch is further provided with a securement 118 that may be removably secured, on one end, to a portion of the sealing section 110 and, on another end, to a desired location such as a portion of a user (e.g., boot or pant leg) or to an object (e.g., a tree branch). One portion of the securement 118 may comprise a lanyard, length of rope or string, or other such device that is dimensioned to permit the lure 114 to contact and drag along a ground surface when connected to the user. As shown in FIG. 2, the pouch 100 may further comprise an aperture 124 for connecting a portion of the securement 118 to the sealing section 110.

The securement 118 may include a pouch connection member 120 for connecting to the sealing section 110 and a user connection member 122 for connecting to a user. The pouch and user connection members 120, 122 allow a user to quickly and easily exchange a used pouch for a new pouch. In particular, after a pouch 100 has been used by the user, it may be replaced by first removing disconnecting the pouch connection member 122 of the used pouch from the user connection member 120 and then connecting the pouch connection member of a new pouch to the user connection member. In certain embodiments, the user connection member 122 includes a first lanyard 140 having a first end 140A and a second end 140B. The first end 140A of the first lanyard 140 passes through the aperture 124 of the sealing section of the pouch 100. Additionally, the pouch connection member 122 includes a connector 142 and a second lanyard 144. The connector 142 has a clasp end 142A and a connection loop 142B mounted to the clasp end 144. The clasp end 142A removably connects to the second end 140B of the first lanyard 140. The second lanyard 144 has a first end 144A and a second end 144B. The first end 144A of the second lanyard 144 is retained in the connection loop 142B of the connector 142. The second end 144B of the second lanyard 144 removably connects to a user-selected location to facilitate the dispersal of the animal attractant. The first lanyard 140 may be selectively detached from the connector 142 and second lanyard 144 while the second lanyard remains connected to the user-selected location.

The pouch 100 may include a pocket 126 formed on an outer surface of at least one of the panels 102, 104 for receiving and securely holding at least a section of the securement 118.

In use, as shown in FIGS. 4A-4F, a user such as a hunter or trapper may attach a pouch to a portion of their clothing such as a pant leg or a boot, which, after the lure is exposed, disperses the attractant as the hunter walks in order to attract an animal to the hunter's location. Alternatively, as shown in FIG. 5, the user may attach the pouch to a location where the dispersal of the attractant is desired. For example, the user may attach the pouch to a tree or bush or to a tree stand, etc., in order to attract an animal to that location.

Figure 4A:
FIG. 4A depicts a user connection member being affixed to a rear portion of a shoe.
Figure 4B:
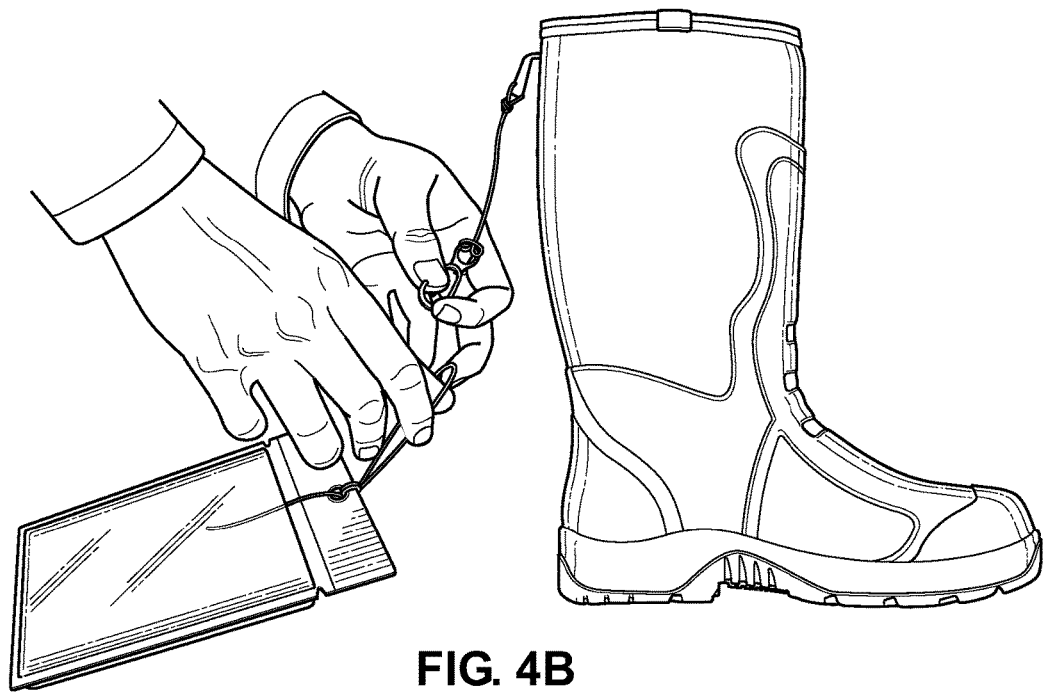
FIG. 4B depicts the user connection member shown in FIG. 4A being connected to a pouch connection member that is secured to a disposable single-use animal attractant dispensing device.
Figure 5:
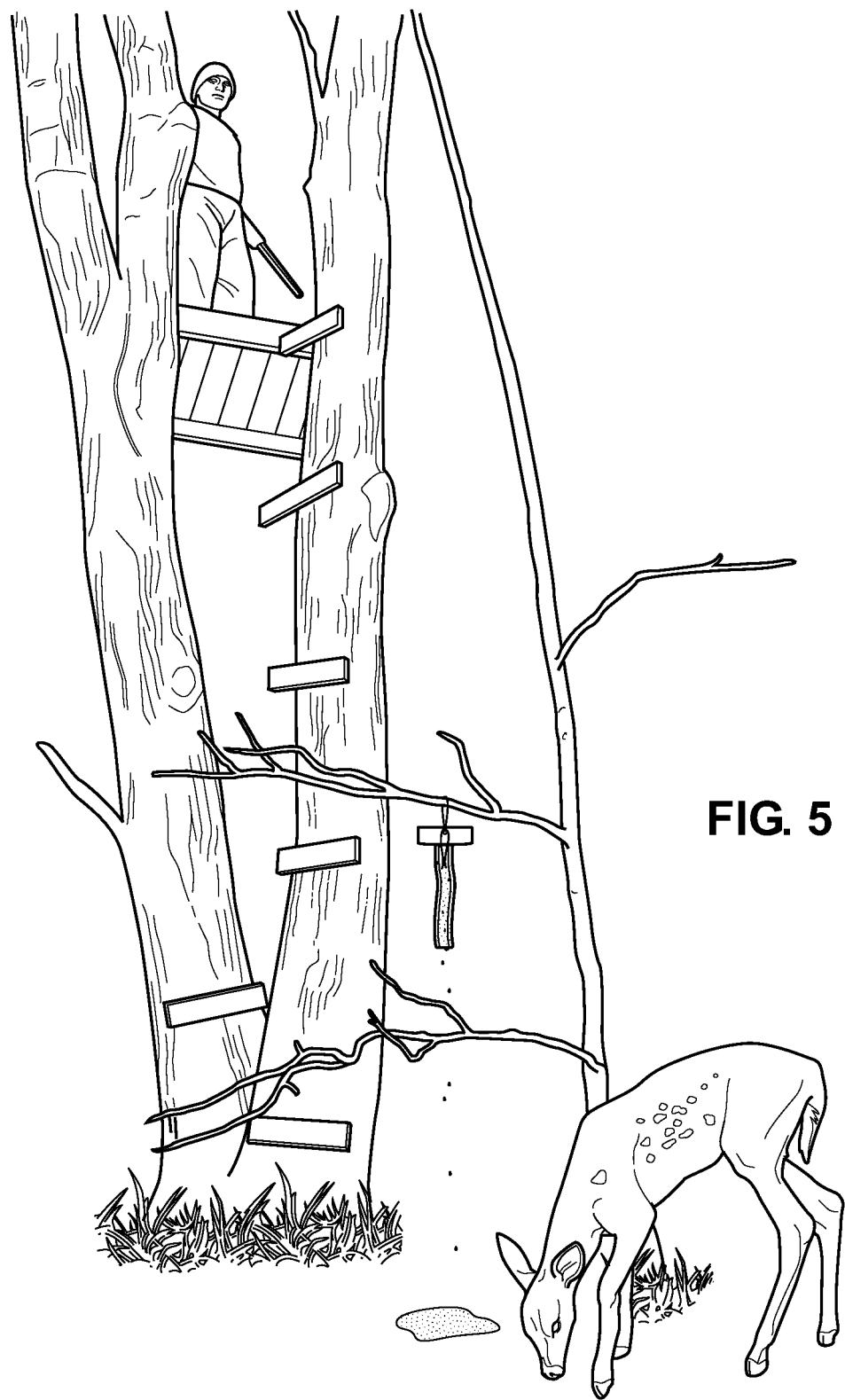
FIG. 5 depicts a disposable single-use animal attractant dispensing device after being secured near the hunter's hunting location away from the hunter.

In particular, FIG. 4A illustrates the user connection member being affixed to a portion of a boot. Next, as shown in FIG. 4B, a pouch is affixed to the user's boot by connecting the user connection member and pouch connection member together. In certain embodiments, two pouches may be used, where one pouch is attached to each shoe. These pouches may include animal attractant that have the same composition or different compositions. For example, it may be preferable to use a male (e.g., buck) scent on one shoe and a female (e.g., doe) scent on the other shoe to replicate the trail of a male following the female.

Figure 4C:
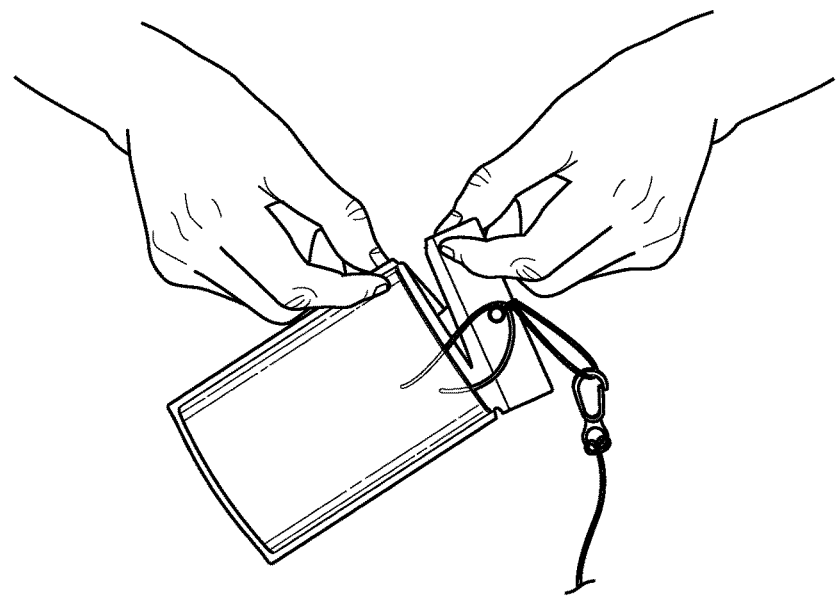
FIG. 4C depicts the disposable single-use animal attractant dispensing device of FIG. 4C with the rupturable seal partially broken.
Figure 4D:
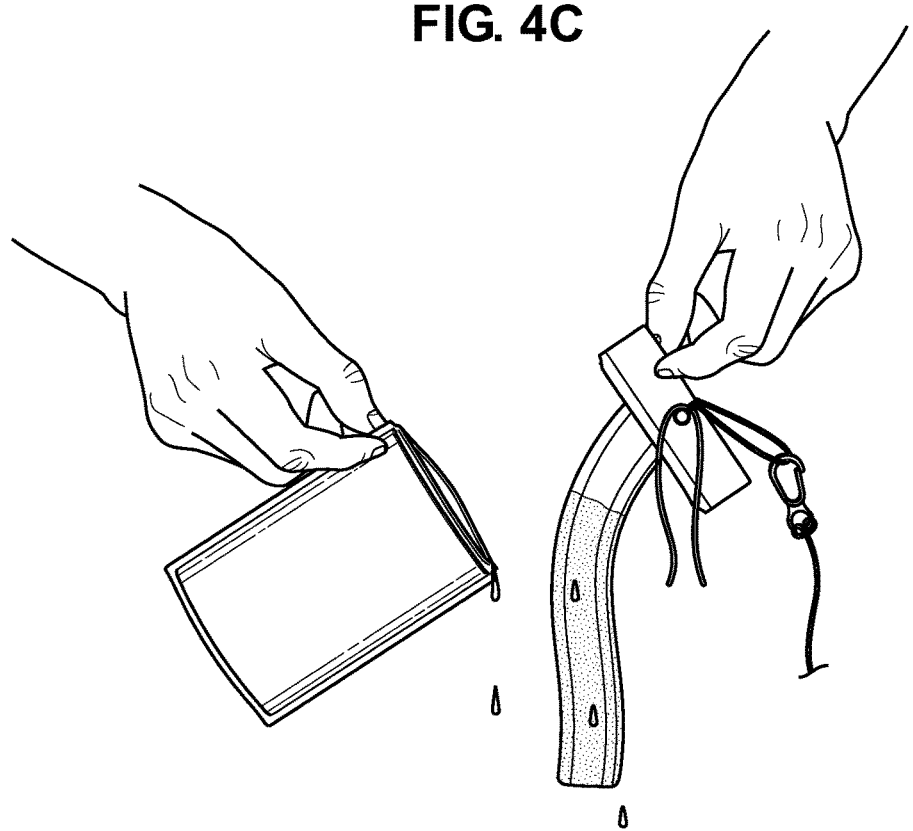
FIG. 4D depicts the disposable single-use animal attractant dispensing device of FIG. 4C with the rupturable seal fully broken and the pouch section separated from the sealing section and lure.
Figure 4E:
FIG. 4E depicts the disposable single-use animal attractant dispensing device of FIG. 4D in use to form a trail of animal attractant along the ground.
Figure 4F:
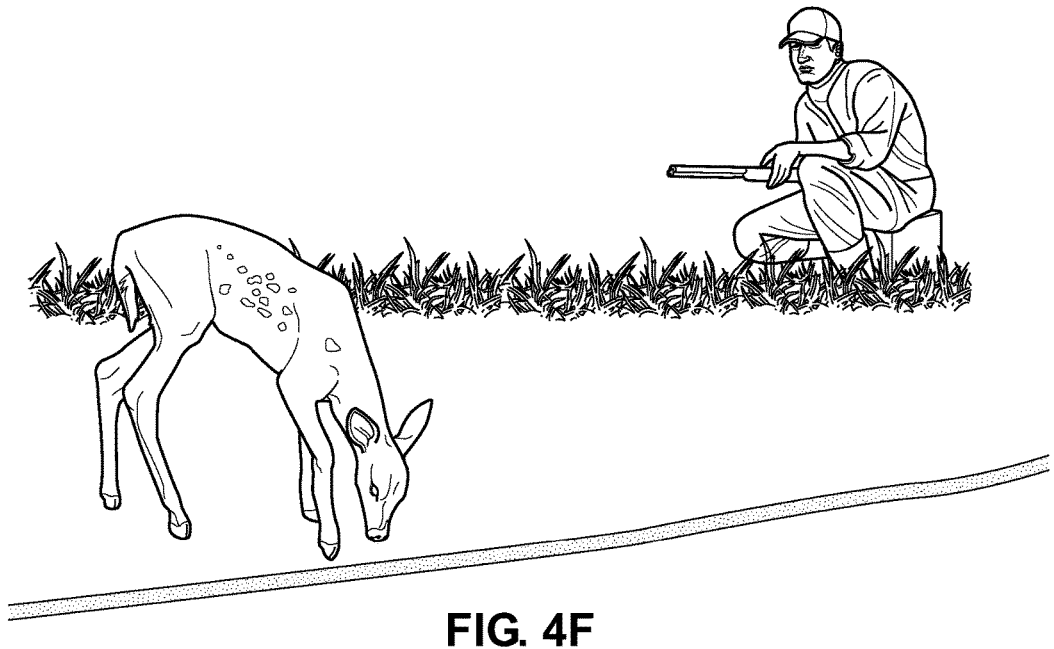
FIG. 4F depicts the trail of animal attractant attracting an animal.

Next, as depicted in FIGS. 4C and 4D, once the pouch is attached to the desired location, the user then tears the pouch open and separates the pouch section from the sealing section to expose the lure. As shown in FIG. 4E, if the pouch is attached to the user's person, after exposing the lure, the user may then walk to the desired hunting location while dragging the lure behind. This dragging action causes the attractant to be dispensed on the ground, on the natural surroundings and in the atmosphere (i.e., air) and creates a trail to the user's hunting location. Ideally, as shown in FIG. 4F, the intended prey will follow this trail to the user's location.

One primary benefit of this design is the avoidance of contact between the user and the attractant. In particular, by attaching the securement to an external portion of the pouch (i.e., to the sealing section), the pouch may be opened, the lure removed from the pouch and placed into use, and also removed after use, all without the user ever coming into contact with the attractant. Accordingly, this provides a clean and simple alternative to prior animal attractant lures and avoids contamination of the user's skin, clothing and/or boot by the attractant.

The various embodiments of the pouch 100 described herein provide a convenient package to enable the clean display and storage of multiple packs of lures including, for example, in a store display or storage room. Other advantages of the pouch 100 design is that the user may place one or more pouches in their pocket, bag, etc., for example, which allows users to easily access the pouch and easily and quickly swap a used lure with a new lure. Another benefit is that the user can utilize and replace the lure(s) without the need to contact the attractant and without having to store a supply of attractant to refill the lure.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An animal attractant dispensing device, the device comprising:
a pouch comprising:
front and back panels disposed in face-to-face relationship with peripheral edges of the panels joined together to define a disposable single-use pouch, wherein the disposable single-use pouch comprises:
a pouch section defined by a section of the peripheral edges of the front and back panels joined together, the pouch section also including a first opening defined by a section of the peripheral edges of the front and back panels not joined together;
a sealing section having an aperture formed therein for receiving a securement, the sealing section formed by sealing together the peripheral edges and a section of the front and back panels located at the first opening; and
a rupturable seal disposed between the sealing section and the pouch section, wherein removing the sealing section from the pouch section ruptures the rupturable seal and exposes the first opening of the pouch section;
a quantity of animal attractant disposed in the pouch section;
a disposable single-use lure comprising a first section comprising an absorbent material for absorbing at least a portion of the quantity of the animal attractant disposed within the pouch section and a second section that is sealed between the front and back panels of the sealing section to fixedly secure the lure to the sealing section; and
a two-part securement configured for attachment to an external portion of the pouch and to allow the pouch to be removably secured at a user-selected location without rupturing the rupturable seal, the securement comprising:
a pouch connection member having a first end and a second end, the first end passing through the aperture for fixedly attaching the pouch connection member to the sealing section of the pouch; and
a user connection member for removably attaching to the pouch connection member, the user connection member having a first end having a connector for removably connecting to the second end of the pouch connection member and a second end for removably connecting to a user-selected location to facilitate the dispersal of the animal attractant, wherein the pouch and pouch connection member may be detached while the user connection member remains connected to the user-selected location.

2. The animal attractant dispensing device of claim 1 further including a pocket formed on an outer surface of at least one of the front and back panels for receiving and securely holding at least a section of the securement, wherein the pocket provides a storage location for the securement that is isolated from the animal attractant and that permits the securement to be accessed without opening the pouch.

3. The animal attractant dispensing device of claim 1, wherein the animal attractant consists of animal urine.

4. The animal attractant dispensing device of claim 3, wherein the animal attractant consists of deer urine.

5. The animal attractant dispensing device of claim 1, wherein the animal attractant comprises a powder attractant.

6. The animal attractant dispensing device of claim 1, wherein the pouch is formed using a material that is substantially impervious to at least one of ultraviolet radiation and visible light.

7. The animal attractant dispensing device of claim 1 further including a tear notch disposed in at least one of the peripheral edges of the joined front and back panels adjacent the rupturable seal, the tear notch operable for assisting a user in rupturing the rupturable seal and in separating the pouch section from the sealing section.

8. An animal attractant dispensing device, the device comprising:
  a pouch comprising:
    front and back panels disposed in face-to-face relationship with peripheral edges of the panels joined together to define a disposable single-use pouch, wherein the disposable single-use pouch comprises:
      a pouch section defined by a section of the peripheral edges of the front and back panels joined together, the pouch section also including a first opening defined by a section of the peripheral edges of the front and back panels not joined together;
      a sealing section having an aperture formed therein for receiving a securement, the sealing section formed by sealing together the peripheral edges and a section of the front and back panels located at the first opening; and
      a rupturable seal disposed between the sealing section and the pouch section, wherein removing the sealing section from the pouch section ruptures the rupturable seal and exposes the first opening of the pouch section;
  a quantity of animal attractant disposed in the pouch section;
  a disposable single-use lure comprising a first section comprising an absorbent material for absorbing at least a portion of the quantity of the animal attractant disposed within the pouch section and a second section that is sealed between the front and back panels of the sealing section to fixedly secure the lure to the sealing section; and
a securement configured for attachment to an external portion of the pouch and to allow the pouch to be removably secured at a user-selected location without rupturing the rupturable seal, the securement comprising:
  a first lanyard having a first end and a second end, the first end of the first lanyard passing through the aperture of the sealing section of the pouch;
  a connector having a clasp end and a connection loop mounted to the clasp end, the clasp end configured for removable connection to the second end of the first lanyard;
  a second lanyard having a first end and a second end, the first end of the second lanyard retained in the connection loop of the connector and the second end of the second lanyard configured for removably connecting to a user-selected location to facilitate the dispersal of the animal attractant,
  wherein the pouch first lanyard may be selectively detached from the connector and second lanyard while the second lanyard remains connected to the user-selected location.

* * * * *